(12) United States Patent
Kinoshita

(10) Patent No.: US 8,293,220 B2
(45) Date of Patent: Oct. 23, 2012

(54) HAIR COSMETIC

(75) Inventor: Koichi Kinoshita, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/322,565

(22) PCT Filed: May 27, 2010

(86) PCT No.: PCT/JP2010/058988
§ 371 (c)(1), (2), (4) Date: Dec. 14, 2011

(87) PCT Pub. No.: WO2010/137645
PCT Pub. Date: Dec. 2, 2010

(65) Prior Publication Data
US 2012/0082633 A1    Apr. 5, 2012

(30) Foreign Application Priority Data

May 28, 2009   (JP) ................................. 2009-129459

(51) Int. Cl.
*A61K 8/00* (2006.01)
*A61K 8/44* (2006.01)
*A61Q 5/02* (2006.01)

(52) U.S. Cl. ................. 424/70.28; 424/70.21; 424/70.1; 424/70.22; 510/424; 510/426

(58) Field of Classification Search .......................... None
See application file for complete search history.

(56) References Cited

U.S. PATENT DOCUMENTS

| 5,346,973 A | 9/1994 | Feustel et al. |
| 2003/0161808 A1 | 8/2003 | Bigorra Llosas et al. |
| 2004/0146478 A1 | 7/2004 | Queralt et al. |

FOREIGN PATENT DOCUMENTS

| JP | 2000191454 A | 7/2000 |
| JP | 2002527373 A | 8/2002 |
| JP | 2002348232 A | 12/2002 |
| JP | 2003535108 A | 11/2003 |
| JP | 2004527550 A | 9/2004 |
| JP | 2007112787 A | 5/2007 |
| JP | 2008208323 A | 9/2008 |
| JP | 2008255053 A | 10/2008 |
| JP | 2009132625 A | 6/2009 |
| WO | 94/21771 A1 | 9/1994 |
| WO | 00/21502 A1 | 4/2000 |

OTHER PUBLICATIONS

International Search Report mailed on Aug. 10, 2010, in corresponding International Application No. PCT/JP2010/058986.
International Preliminary Report on Patentability mailed on Dec. 22, 2011, in corresponding International Application No. PCT/JP2010/058988.

*Primary Examiner* — Robert A Wax
*Assistant Examiner* — Randeep Singh
(74) *Attorney, Agent, or Firm* — Andrew F. Young, Esq.; Lackenbach Siegel, LLP

(57) ABSTRACT

The present invention provides a hair cosmetic composition contains (A) a di-long-chain cationic surfactant represented by formula (1); (B) an ethylene oxide adduct of 1,2-alkanediol represented by formula (2) and/or an N-acyl-N-methylmonoethanolamide represented by formula (3); and (C) a hydrophobicized alkyl cellulose represented by formula (4) and/or a cationic polymer represented by formula (5), and (D) water (chemical formulas not shown). The hair cosmetic composition has remarkably high safety and excellent stability. In addition, the composition exhibits excellent spreadability over hair upon application thereof and can finish hair with suppleness and less stickiness. Also, even when the composition has a low base material content, a lamellar liquid crystal structure can be formed. Quite surprisingly, the hair cosmetic composition can provide hair with conditioning effects together with excellent viscoelasticity and shows such excellent performance as to cause no problem even though the rinsing step is omitted.

9 Claims, No Drawings

HAIR COSMETIC

TECHNICAL FIELD

The present invention relates to a hair cosmetic composition and, more particularly, to a hair cosmetic composition suitable for serving as a hair conditioner, a hair rinse, or a rinse-in-shampoo.

BACKGROUND ART

Currently, various types of hair cosmetic compositions for giving conditioning effects to hair are provided in consideration of sensation in use, ease of use, safety, etc. of users.

For example, Patent Document 1 discloses a hair cosmetic composition which contains a di-long-chain cationic surfactant, a hydrophobically modified alkylcellulose, and a higher alcohol and which forms a rinse-like gel. The hair cosmetic composition disclosed in Patent Document 1 is stable over passage of time and is suitable for serving as a hair conditioner or a hair treatment. Patent Document 2 discloses a transparent or semi-transparent conditioning composition which contains a cationic surfactant, an anionic or amphoteric polymer, and an aqueous carrier and which forms a water-insoluble complex upon dilution thereof. Patent Document 3 discloses a conditioning composition which contains a cationic surfactant, an anionic or amphoteric polymer, a high-melting-point aliphatic compound, and an aqueous carrier and which forms a gel matrix. Patent Document 4 discloses a conditioning composition which contains a cationic surfactant, an anionic or amphoteric polymer, a conditioning agent, and an aqueous carrier and which forms a water-insoluble complex between the surfactant system and the polymer.

Patent Document 5 discloses a preparation which contains a di-long-chain cationic surfactant (esterquat), an oil ingredient, and a lower alcohol, which is readily spreadable upon application, and which is rapidly absorbed without remaining residues thereof. Patent Document 6 discloses a mixture of di-long-chain cationic surfactants (esterquat) having different acyl group lengths. Patent Document 7 discloses a hair-care preparation which contains a natural oil including sterol and an unsaturated fatty acid in specific amounts.

Patent Document 8 discloses an aqueous hair cosmetic composition which contains a sucrose fatty acid ester, a cationic surfactant, a silicone, ethanol, and water and which exhibits high volatility after application, and provides hair with moistness even after volatilization of the composition.

Patent Document 9 and other documents disclose a hair cosmetic composition containing a carboxyvinyl polymer or an alkyl-modified carboxyvinyl polymer, which composition assumes milky lotion or cream and is used in a leave-on manner (i.e., use without rinsing off the composition).

PRIOR ART DOCUMENTS

Patent Documents

Patent Document 1: Japanese Patent Application Laid-Open (kokai) No. 2007-112787
Patent Document 2: Japanese Kohyo (PCT) Patent Publication No. 2008-543949
Patent Document 3: Japanese Kohyo (PCT) Patent Publication No. 2008-543952
Patent Document 4: Japanese Kohyo (PCT) Patent Publication No. 2008-546806
Patent Document 5: Japanese Kohyo (PCT) Patent Publication No. 2002-527373
Patent Document 6: Japanese Kohyo (PCT) Patent Publication No. 2003-535108
Patent Document 7: Japanese Kohyo (PCT) Patent Publication No. 2004-531565
Patent Document 8: Japanese Patent Application Laid-Open (kokai) No. 2005-330214
Patent Document 9: Japanese Patent Application Laid-Open (kokai) No. 2005-89366

SUMMARY OF THE INVENTION

Problems to be Solved by the Invention

As described above, a variety of hair cosmetic compositions for giving conditioning effects to hair have been provided. However, such hair cosmetic compositions are desired to be improved for higher performance. Thus, an object of the present invention is to provide a hair cosmetic composition which provides hair with conditioning effects, which ensures improved safety to hair and the scalp and skin to such a degree that the composition is not required to be rinsed off after application thereof to hair, which attains improved sensation in use after application thereof to hair, and which is stable over passage of time.

The aforementioned hair cosmetic composition disclosed in Patent Document 1 is stable over passage of time and can form a rinse-like gel. In order to enhance stability, a higher alcohol is incorporated as an essential ingredient into the composition. The invention of Patent Document 1 is directed to a technique of enhancing stability of the composition in the presence of a higher alcohol. However, the stability of products from the composition remains unsatisfactory. That is, the stability of the composition is unsatisfactory at high and low temperatures. More specifically, lauryl alcohol, which is a typical example of the higher alcohol that effectively forms an associated product with ingredient (A), leads to poor stability at high temperature and provides the skin with irritation, which is not preferred. Furthermore, when the length of an alkyl chain of higher alcohol is prolonged (e.g., use of stearyl alcohol or behenyl alcohol) to improve high-temperature stability, the formed higher alcohol-ingredient (A) association has poor viscoelasticity and poor stability at low temperature. In order to solve the problems, attempts have been made to incorporate an associating thickener containing a hydrophobe modified cellulose derivative into a hair cosmetic composition. However, the thus-prepared composition has poor stability at high temperature, which is problematic.

Some of the aforementioned compositions contain esterquat. Although the compositions as described above assumes cream to milky lotion by virtue of the presence of a higher alcohol, the other compositions are a liquid composition having very low viscosity or a composition whose viscosity has been enhanced by only a polymer thickener. Such a low-viscosity composition does not meet the users' demand, while such a composition whose viscosity has been enhanced by only a polymer thickener provides sticky and stiff sensation due to the polymer and cannot suppress irritation to the skin due to the cationic surfactant. Generally, cationic surfactants are known to give intense irritation to the skin, and such irritation is usually mitigated by use of a co-surfactant such as higher alcohol in combination. Among cationic surfactants, esterquat is preferred, since it gives less irritation to the skin. However, as described above, a combination of esterquat and higher alcohol is not preferred, from the viewpoints of stability and other factors. Hitherto, there has been found no co-surfactant which is used in combination with esterquat and which provides such a composition with stability and skin safety higher than those attained by a higher alcohol.

Also, into a composition containing a carboxyvinyl polymer or an alkyl-modified carboxyvinyl polymer, a cationic surfactant for imparting suppleness and smoothness to hair cannot stably incorporated. Therefore, an oil ingredient (e.g., silicone) or a polyhydric alcohol is incorporated into such a composition, with the view of imparting suppleness to hair. However, the composition does not provide hair with satisfactory suppleness and imparts poor smoothness to hair.

Means for Solving the Problems

The present invention has been accomplished in order to solve the aforementioned problems. Accordingly, the present invention provides a hair cosmetic composition comprising the following ingredients (A), (B), (C), and (D):

(A) a di-long-chain cationic surfactant represented by formula (1):

[F1]

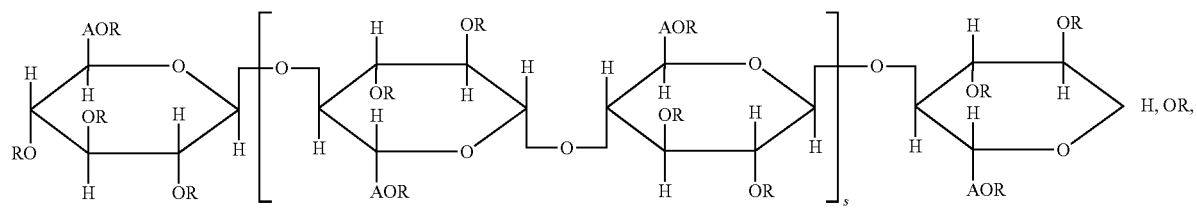

wherein each of $R^aCOs$, which may be identical to or different from each other, represents an aliphatic acyl group having 10 to 22 carbon atoms and 0 to 3 double bonds; p is an integer of 1 to 3; and X represents a halogen atom, metosulfate, or metophosphate;

(B) an ethylene oxide adduct of 1,2-alkanediol represented by formula (2):

[F2]

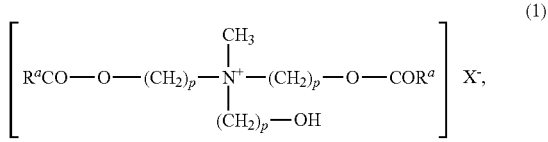

wherein $R^b$ represents a hydrocarbon group having 8 to 20 carbon atoms and 0 to 2 double bonds; each of m and n, which represent amount by mol of added ethylene oxide, is an integer of 0 to 2; and the average of m+n is greater than 0 and smaller than 2; and/or an N-acyl-N-methylmonoethanolamide represented by formula (3):

[F3]

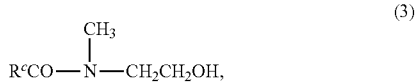

wherein $R^c$ represents a hydrocarbon group having 9 to 21 carbon atoms and 0 to 2 double bonds;

(C) a hydrophobicized alkyl cellulose represented by formula (4):

[F4]

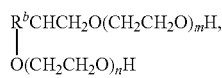

wherein R represents a bonding group $R^1$-$R^2$; a plurality of $R^1$s, which may be identical to or different from one another, represent at least one group selected from among —[$CH_2CH(CH_3)O$]$_r$—, —[$CH_2CH_2O$]$_r$—, and —[$CH_2CH(OH)CH_2O$]$_r$— (wherein r is an integer of 0 to 4); $R^2$ represents at least one group selected from among a C12 to C28 hydrocarbon group, a hydrogen atom, and a C1 to C4 alkyl group, with at least one $R^2$ being a C12 to C28 hydrocarbon group; A represents a group —($CH_2$)$_t$— (wherein t is an integer of 1 to 3); and s is a number of 100 to 10,000; and/or a cationic polymer represented by formula (5):

[F5]

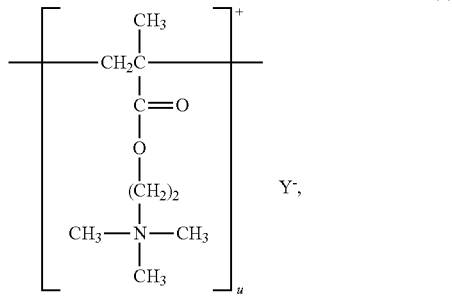

wherein Y represents a halogen atom, and u represents the number of bonded quaternary ammonium unit(s); and (D) water.

Effects of the Invention

The hair cosmetic composition of the present invention has remarkably high safety and excellent stability. In addition, the composition exhibits excellent spreadability over hair upon application thereof and can finish hair with more suppleness and less stickiness. Also, even when the composition has a low base material content, a lamellar liquid crystal structure can be formed. Quite surprisingly, the hair cosmetic composition can provide hair with conditioning effects together with excellent viscoelasticity and shows such excellent performance as to cause no problem even though the rinsing step is omitted. Specifically, the composition is suitably employed as a hair rinse, a hair conditioner, a hair treatment, a rinse-in-shampoo, etc., and can be used with or without rinsing.

MODES FOR CARRYING OUT THE INVENTION

As described above, the hair cosmetic composition of the present invention contains, as essential ingredients, (ingredient (A)) a di-long-chain cationic surfactant (1), (ingredient (B)) an ethylene oxide adduct of 1,2-alkanediol (2) (B-1) and/or an N-acyl-N-methylmonoethanolamide (3) (B-2), (ingredient (C)) hydrophobicized alkyl cellulose (4) (C-1) and/or a specific cationic polymer (5) (C-2), and (ingredient D) water.

[Ingredient (A)]

Ingredient (A) is a di-long-chain cationic surfactant (1).

In formula (1), $R^a CO$ represents an aliphatic acyl group having 10 to 22 (preferably 12 to 16, most preferably 12) carbon atoms and 0 to 3 double bonds; p is a number of 0 to 3; when p is 0, the group $—(CH_2)_p—OH$ represents a methyl group; and X represents a halogen atom, metosulfate, or metophosphate.

Examples of ingredient (A) include dicocoylethyl hydroxyethylmonium metosulfate, dipalmitoylethyl hydroxyethylmonium metosulfate, and distearylethyl hydroxyethylmonium chloride. Preferably, ingredient (A) is a halide or metosulfate of a coconut fatty acid-based esterquat. When the aliphatic acyl group $R^a CO$ is a long-carbon-chain group, the stability of the composition at low temperature is poor. Examples of the commercial product of preferred ingredient (A) include Dehyquart L80 (product of Cognis Japan) (dicocoylethyl hydroxyethylmonium metosulfate).

The ingredient (A) content of the hair cosmetic composition is preferably 0.1 to 5 mass %, more preferably 0.3 to 2 mass %. When the ingredient (A) content of the hair cosmetic composition is less than 0.1 mass %, hair conditioning effects and viscosity of the composition are prone to be poor, and the long-term stability of the composition particularly at low temperature is prone to decrease. When the content is in excess of 5 mass %, the composition has poor safety to the scalp and skin in the case where rinsing is omitted.

[Ingredient (B)]

Ingredient (B) is an ethylene oxide adduct of 1,2-alkanediol (2) (B-1) and an N-acyl-N-methylmonoethanolamide (3) (B-2). One or more members of ingredient (B) may be incorporated into the hair cosmetic composition of the present invention.

<Ingredient (B-1)>

Hereinafter, the above 1,2-alkanediol ethylene oxide (EO) adduct (2) may be referred to as "EO-alkalnediol" or "EO (average of the numbers of bonded EO units) alkanediol."

In formula (2), $R^b$ represents a hydrocarbon group having 8 to 20 (preferably 10 to 14, most preferably 10) carbon atoms. In other words, $R^b CHCH_2$ has 10 to 22 (preferably 12 to 16, most preferably 12) carbon atoms. The number of added ethylene oxide units, represented by m or n, is an integer of 0 to 2. The average of m+n (the average of the sum of m and n) is greater than 0 and smaller than 2. Preferably, the average of the sum of m and n is not less than 0.5 nor more than 1.5 (the average of m+n is 0.5 to 1.5).

<Ingredient (B-2)>

In formula (3), $R^c$ represents a hydrocarbon group having 9 to 21 (preferably 11 to 15, most preferably 11) carbon atoms. In other words, $R^c CO$ has 10 to 22 (preferably 12 to 16, most preferably 12) carbon atoms. For example, coconut fatty acid diethanolamide (see the Examples) has a coconut fatty acid group corresponding to $R^c CO$ having 12 carbon atoms and exemplified as a preferred species of N-acyl-N-methylmonoethanolamide (3).

Generally, the ethylene oxide adduct of 1,2-alkanediol (2) has higher safety to the scalp and skin, as compared with the N-acyl-N-methylmonoethanolamide (3).

<Amounts>

Regarding ingredient (B), the amount of ethylene oxide adduct of 1,2-alkanediol (2) or N-acyl-N-methylmonoethanolamide (3) or the total amount thereof is preferably 0.5 to 20 mass %, more preferably 1 to 5 mass %, with respect to the entirety of the hair cosmetic composition. When the amount of ingredient (B) with respect to the entirety of the hair cosmetic composition is less than 0.5 mass %, the composition has insufficient viscosity and elasticity at ambient temperature, whereas when the amount is in excess of 20 mass %, the composition has poor stability in the appearance at low temperature, and poor safety to the scalp and skin in the case where rinsing is omitted.

[Ingredient (C)]

Ingredient (C) includes the aforementioned hydrophobicized alkyl cellulose (4) (C-1) and cationic polymer (5) (C-2). One or more members of ingredient (C) may be incorporated into the hair cosmetic composition of the present invention.

<Ingredient (C-1)>

The hydrophobicized alkyl cellulose (4) serving as ingredient (C-1) is a water-soluble cellulose ether derivative into which a hydrophobic long-chain alkyl group has been incorporated. The hair cosmetic composition of the present invention may contain one or more members of ingredient (C).

The hydrophobicized alkyl cellulose (4) of interest may be generally produced through bringing a compound for providing a long-chain alkyl group into contact a water-soluble cellulose ether derivative serving as a main structure in the presence of an alkaline catalyst. Specific examples of the cellulose ether derivative include methyl cellulose (in bonding group $R^1-R^2$ (R), $R^1$ is absence (r=0), and $R^2$ is a hydrogen atom or a methyl group), ethyl cellulose (similarly, $R^1$ is absence, and $R^2$ is a hydrogen atom or an ethyl group), propyl cellulose (similarly, $R^1$ is absence, and $R^2$ is a hydrogen atom or a propyl group), butyl cellulose (similarly, $R^1$ is absence, and $R^2$ is a hydrogen atom or a butyl group), hydroxyethyl cellulose (in bonding group $R^1-R^2$, $R^1$ is group $—[CH_2CH_2O]_r—$ (r=0 or 1, r≧1 in at least one $R^1$), and $R^2$ is a hydrogen atom), hydroxypropyl cellulose (in bonding group $R^1-R^2$, $R^1$ is group $—[CH_2CH(CH_3)O]_r—$ (r is an integer of 0 to 5 (preferably 0 to 3), r≧1 in at least one $R^1$), and $R^2$ is a hydrogen atom), and hydroxypropylmethyl cellulose (in bonding group $R^1-R^2$, $R^1$ is group $—[CH_2CH(CH_3)O]_r—$ (r is an integer of 0 to 5 (preferably 0 to 3), r≧1 in at least one $R^1$), and $R^2$ is a hydrogen atom or a methyl group). Specific examples of the compound for providing a long-chain alkyl group include the following long-chain alkyl glycidyl ether (4'):

[F6]

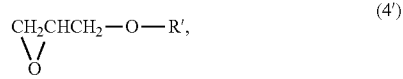

R' represents a C10 to C28 (preferably C12 to C22) alkyl group.

The amount of group —CH$_2$CH(OH)CH$_2$OR' incorporated as a part of Rs into the hydrophobicized alkyl cellulose (4) through the reaction is about 0.1 to about 5.0 mass %, with respect to the amount of the hydrophobicized alkyl cellulose (4). For adjusting the content to fall within the above range, the hydrophobicized alkyl cellulose may be produced through reaction between the water-soluble cellulose ester derivative and the long-chain alkyl glycidyl ether under appropriately selected conditions (e.g., mole ratio in reaction, reaction time, and type of alkaline catalyst). After completion of reaction, the reaction product is subjected to purification steps (e.g., neutralization, filtration, washing, drying, and classification), whereby a hydrophobicized alkyl cellulose (4) suitable for serving as the ingredient of the hair cosmetic composition can be produced. Notably, the method of incorporating an long-chain alkyl group is not limited to the above-described method.

Among the aforementioned water-soluble cellulose ether derivatives, hydroxypropylmethyl cellulose or hydroxyethyl cellulose is preferred, with hydroxypropylmethyl cellulose being particularly preferred (in this case, four Rs in the hydrophobicized alkyl cellulose (4) are a hydrogen atom, a methyl group, a bonding group R$^1$-R$^2$ (R$^1$: —[CH$_2$CH(CH$_3$)O]$_t$—, R$^2$: a hydrogen atom), and a bonding group R$^1$-R$^2$ (R$^1$: —CH$_2$CH(OH)CH$_2$O—, R$^2$: R'); t of A is 1; and A is a methylene group). R' of the long-chain alkyl glycidyl ether (4') is preferably a stearyl group (—C$_{18}$H$_{37}$) or a cetyl group (—C$_{16}$H$_{33}$) (in this case, group —CH$_2$CH(OH)CH$_2$OR' is group —CH$_2$CH(OH)CH$_2$O—C$_{18}$H$_{37}$ or —CH$_2$CH(OH)CH$_2$O—C$_{16}$H$_{33}$).

A hydrophobicized hydroxypropylmethyl cellulose in which R' is a stearyl group is one of the most preferred embodiments of the hydrophobicized alkyl cellulose (4) and is commercially available as a tradename "Sangelose" (product of Daido Chemical Corporation). Such a commercial product may be incorporated into the hair cosmetic composition of the present invention (e.g., Sangelose 90L, 90M, 90H, 60L, 60M, and 60H).

<Ingredient (C-2)>

Examples of the halogen atom Y of the cationic polymer (5) include chlorine, bromine, iodine, and fluorine. Among them, a chlorine atom is preferred. A cationic polymer (5) in which the halogen atom Y is chlorine is known as a trivial name of POLYQUATERNIUM-37 (CAS No. 26161-33-1), which is used as an anti-static agent, a coating agent, a hair-styling agent, etc. One commercial product thereof is Ultragel 300 supplied by Cognis.

<Amount>

In the case where ingredient (C) is ingredient C-1; i.e., a hydrophobicized alkyl cellulose (4), the hair cosmetic composition of the present invention preferably has an ingredient (C) content of 0.01 to 1 mass %, particularly preferably 0.03 to 0.5 mass %, with respect to the entirety of the hair cosmetic composition. When the amount is less than 0.01 mass % with respect to the entirety of the hair cosmetic composition, final products obtained from the composition are likely to have impaired viscosity and poor stability of oil-ingredients in emulsion, whereas when the amount is in excess of 1 mass %, the viscosity of the composition excessively increases, thereby impeding production of hair cosmetic products, and the composition is prone to exhibit poor sensation in use; i.e., sticky and stiff sensation. In the case where ingredient (C) is ingredient C-2; i.e., a cationic polymer (5), the hair cosmetic composition of the present invention preferably has an ingredient (C) content of 0.03 to 2 mass %, particularly preferably 0.05 to 1 mass %, with respect to the entirety of the hair cosmetic composition. When the amount is less than 0.03 mass % with respect to the entirety of the hair cosmetic composition, final products obtained from the composition have low viscosity, whereas when the amount is in excess of 2 mass %, sensation in use of the composition is impaired, to increase sticky and stiff sensation.

In the case where ingredient (C) includes ingredients C-1 and C-2, the hair cosmetic composition of the present invention preferably has a total ingredient (C) content (by mass) of 0.03 to 1.5 mass %, particularly preferably 0.05 to 1 mass %, with respect to the entirety of the hair cosmetic composition.

[Ingredient (D)]

As described above, ingredient (D) is water. Any water such as purified water, ion-exchange water, tap water, or natural water may be used. No particular limitation is imposed on the ingredient (D) content, but it is about 20 to about 95 mass % with respect to the entirety of the hair cosmetic composition and is adjusted such that the hair cosmetic composition of the present invention has appropriate ingredient (A) content, ingredient (B) content, ingredient (C) content, and optional additive content. When the water content is excessively high, each ingredient concentration of the hair cosmetic composition becomes excessively low, failing to fully attain the effects of the present invention, whereas when the water content is excessively low, each compound concentration (other than ingredient (D)) of the hair cosmetic composition becomes excessively high, resulting in mixing failure and loss of raw materials.

[Other Factors]

The amounts of essential ingredients (A) to (D) incorporated into the hair cosmetic composition of the present invention are as described above. These amounts are adjusted in consideration of some other factors.

(1) Regarding the requirements in terms of the number of carbon atoms, the number ($\alpha$1) of the carbon atoms that form R$^a$CO of the di-long-chain cationic surfactant represented by formula (1) (A) and the number ($\alpha$2) of the carbon atoms that form each of R$^b$CHCH$_2$ of the ethylene oxide adduct of 1,2-alkanediol represented by formula (2) (B-1) and R$^c$CO of the N-acyl-N-methylmonoethanolamide represented by formula (3) (B-2) preferably satisfy the relationship: ($\alpha$2−2)≦$\alpha$1≦ ($\alpha$2+2), more preferably, $\alpha$1 is equal to $\alpha$2, from the viewpoint of maintaining the stability of the composition of the present invention at high level.

In an actual situation, each ingredient may be a mixture of the corresponding compounds having different numbers of carbon atoms. Thus, the concept "equal" refers not only to the case where the numbers of carbon atoms of the two species are correctly equal to each other, but also to the case where the numbers of carbon atoms of the most predominant species in the mixtures are equal to each other.

(2) The compositional proportions of ingredients (A) to (D) are more preferably adjusted within the aforementioned ranges such that a lamellar liquid crystal structure is formed in the system. Through incorporation of essential ingredients in amounts falling within the aforementioned preferred ranges, a lamellar liquid crystal structure can be formed in the system. Formation of the lamellar liquid crystal structure may be confirmed through an X-ray scattering method (small angle: SAXS, wide angle: WAXS), observation under a polarization microscope, FF-TEM observation, or the like. In the case of SAXS measurement, the intensity of X-ray source obtained by a conventional commercial apparatus may be insufficient. In such a case, the structure can be confirmed by prolonging irradiation time in, for example, a large-scale radiation facility.

(3) The viscosity of the hair cosmetic composition of the present invention, as measured by means of a Brookfield viscometer, is preferably 1,500 to 30,000 [mPa·s] (30° C.). When the viscosity is less than 1,500 [mPa·s] or in excess of 30,000 [mPa·s], spreadability of the sample over hair is poor. Through incorporation of essential ingredients in amounts falling within the aforementioned preferred ranges, the viscosity of the system can fall within the target range.

[Incorporation of Other Ingredients]

(1) Incorporation of oil ingredients

So long as the effects of the present invention are not impaired, the hair cosmetic composition of the present invention may further contain other additional ingredients. To the hair cosmetic composition of the present invention, an oil ingredient, particularly silicone oil, is thought to be added to provide cosmetic products. Generally, when a cosmetic product containing an oil ingredient is applied, sticky sensation is provided. However, according to the hair cosmetic composition of the present invention, such sticky sensation is suppressed, and smoothness is remarkably effectively imparted to hair after drying hair. In other words, in the hair cosmetic composition of the present invention, advantages of an oil ingredient can be fully attained, while problems involved in use thereof is solved.

Examples of the oil ingredient (silicone oil) include methylpolysiloxane, methylphenylpolysiloxane, silicone resin, octamethylcyclotetrasiloxane, decamethylcyclopentasiloxane, methylpolycyclosiloxane, methylhydrogenpolysiloxane, dimethylsiloxane.methyl(POE)siloxane copolymer, dimethylsiloxane.methyl(POE)siloxane.methyl(POP)siloxane copolymer, dimethylsiloxane.methylstearoxysiloxane copolymer, methylpolysiloxane emulsion, cyclic silicone resin, highly polymerized methylpolysiloxane, dimethylsiloxane.methyl(POP)siloxane copolymer, tetradecamethylhexasiloxane, octamethyltrisiloxane, dodecamethylcyclohexasiloxane, dimethylsiloxane-methylcetyloxysiloxane copolymer, amino-modified silicone (e.g., amodimethicone, aminopropylmethicone), polyether-modified silicone, PEG amodimethicone, and PCA dimethicone. Examples of the oil ingredient also include fats and oils (liquid) (e.g., olive oil, camellia oil, macadamia nut oil, and castor oil); fats and oils (solid); waxes (e.g., carnauba wax, candelilla wax, jojoba oil, beeswax, and lanolin); hydrocarbon oils (e.g., liquid paraffin, paraffin, petrolatum, ceresin, microcrystalline wax, and squalane); higher fatty acids (e.g., lauric acid, myristic acid, palmitic acid, stearic acid, and isostearic acid); ester oils (e.g., isopropyl myristate, 2-octyldodecyl myristate, cetyl 2-ethylhexanoate, and diisostearyl malate); and higher alcohols (e.g., cetyl alcohol, stearyl alcohol, and isostearyl alcohol).

No particular limitation is imposed on the amount of the above oil ingredient incorporated into the hair cosmetic composition of the present invention, and the amount, inclusive of type and combination, of the oil ingredient are appropriately selected in accordance with form, purpose of use, etc. of specific products. In order to fully attain the aforementioned advantages of the hair cosmetic composition of the present invention, the amount of oil ingredient (in the case of silicone oil) is preferably adjusted to about 0.1 to about 30 mass % with respect to the entirety of the hair cosmetic composition.

The amount of an oil ingredient other than silicone oil is preferably about 0.01 to about 5 mass % with respect to the entirety of the hair cosmetic composition.

(2) Common Ingredients Other than Oil Ingredient

In addition to the aforementioned oil ingredients, if needed, the hair cosmetic composition of the present invention may further contain an ingredient commonly used in cosmetics. Examples of such ingredients include powder ingredients (e.g., mica, talc, kaolin, alcium carbonate, magnesium carbonate, silicic anhydride, aluminum oxide, barium sulfate, red ron oxide, yellow iron oxide, black iron oxide, chromium oxide, ultramarine, iron blue, carbon lack, titanium dioxide, zinc oxide, titanated mica, fish scale flake, bismuth oxychloride, boron nitride, photochromic pigments, synthetic fluorphlogopite, iron-containing synthetic fluorphlogopite, and composite microparticle powder); surfactants (other than ingredients (A) and (B)); humectants (e.g., glycerin, propylene glycol, dipropylene glycol, 1,3-butylene glycol, polyethylene glycol, sorbitol, sodium 2-pyrrolidone-5-carboxylate, and sodium hyaluronate); water-soluble polymers (e.g., cationized polysaccharides such as cationized cellulose, cationized guar gum, and cationized locust bean gum; synthetic cationic polymers such as polyquaternium-7; and amphoteric polymers such as polyquaternium-39); thickeners (e.g., plant-derived thickeners, microorganism-derived thickeners, animal-derived thickeners, cellulose-derived thickeners, starch-derived thickeners, alginic acid-derived thickeners, vinylic polymers, and high-molecular-weight polyethylene glycol); UV-absorbers; sequestering agents; lower alcohol; polyhydric alcohols; sugars; amino acids; organic amines; polymer emulsions; pH-regulators; skin nutrients; vitamins; anti-oxidants; anti-oxidant aids; various extracts; antiseptic agents (e.g., methylparaben, ethylparaben, propylparaben, phenoxyethanol, sodiumbenzoate, 1,2-octanediol, and methylisothiazolinone); pigments (e.g., Red No. 106, Orange No. 205, Yellow No. 4, Green No. 3, and Blue No. 1); and a perfume.

[Hair Cosmetic Composition of the Present Invention]

The hair cosmetic composition of the present invention is suitably employed as, for example, a hair rinse, a hair conditioner, a hair treatment, or a rinse-in-shampoo. Regarding conventional hair cosmetic compositions employed in general products of hair rinse, hair treatment, rinse-in-shampoo, etc., in a typical mode of use, a product of interest is applied to hair, and the applied product is rinsed off immediately after application or after maintenance with hair for a while. However, the hair cosmetic composition of the present invention does not leave unpleasant sensation to users and is free from irritation to the scalp and skin, even though the rinsing step is omitted, and hair conditioning effects can be substantially enhanced. Furthermore, in the case where the rinsing step is omitted, environmental load ($CO_2$ emission) due to use of hot water for rinsing is drastically reduced, and utility cost can be reduced.

EXAMPLES

The present invention will next be described by way of Examples, which should not be construed as limiting the invention thereto. Unless otherwise specified, the amount of an ingredient is on the basis of mass % with respect to the entire amount of the target into which the ingredient is incorporated.

[Details of Tests]

The test methods employed for evaluating test products in the Test Examples, and test results will be described. Tables 1 and 2 show the formulations of the tested products (Test Examples 1 to 23), and the test results. Each of the test products (Test Examples 1 to 20) shown in Table 1 was prepared by adding the ingredients to heated water (70° C.) under stirring, and cooling the mixture to 30° C. Each of the test products (Test Examples 21 to 23) shown in Table 2 was prepared by mixing, in ion-exchange water, ingredients other than ion-exchange water at a temperature higher than that of the melting point of each ingredient, and cooling the mixture to room temperature.

(1) Stability Test
<Viscosity>

Each of the thus-prepared test products was placed in a sample bottle, and the bottle was closed with a cap. The sample bottle was allowed to stand in a thermostat bath maintained at 30° C., and then the viscosity thereof was measured by means of a Brookfield viscometer. Viscosity measurement was performed after rotation of the test product at 12 rpm for one minute. When a test product exhibits a viscosity lower than 1,500 [mPa·s], the test product is regarded as a Comparative Example product.

<Stability in Appearance>

Each of the thus-prepared test products was placed in a sample bottle, and the bottle was closed with a cap. The sample bottle was allowed to stand for two weeks at 55° C. or 5° C. The appearance of the test product was visually observed, and the appearance was evaluated on the basis of the following ratings.

◯: Virtually the same appearance and viscosity as those of the product stored at room temperature
X: Viscosity or appearance considerably different from that of the product stored at room temperature (2) Actual Use Test Eight expert panelists evaluated tactile sensation upon application of each Test Example sample after rising off the shampoo (i.e., "suppression of sticky sensation of hair" upon application of sample to hair). Also, the panelists evaluated "smoothness" and "suppleness" after drying, specifically, after rinsing off the shampoo, applying each Test Example sample to hair, and drying hair without rinsing off the applied sample. The evaluation criteria for each of the test items are as follows.

<Suppression of Sticky Sensation Upon Application of Sample>

◯: Six or more panelists responded "less sticky"
Δ: Three to five panelists responded "less sticky"
X: Two or less panelists responded "less sticky"

<Smoothness after Drying>

◯: Six or more panelists responded "smooth"
Δ: Three to five panelists responded "smooth"
X: Two or less panelists responded "smooth"

<Suppleness after Drying>

◯: Six or more panelists responded "supple hair"
Δ: Three to five panelists responded "supple hair"
X: Two or less panelists responded "supple hair"

TABLE 1

| Ingredients | Test Ex. 1 | 2 | 3 | 4 | 5 | 6 | 7 |
|---|---|---|---|---|---|---|---|
| | Amount (mass %) * blank: none | | | | | | |
| Dehyquart L80 | | 2.0 | 2.0 | 2.0 | 2.0 | 2.0 | 2.0 |
| Stearyl trimethyl ammonium chloride | 0.3 | | | | | | |
| POE(1.0)-1,2-dodecanediol | 3.0 | 3.0 | 3.0 | 3.0 | 1.0 | | 3.0 |
| Aminon C-11S | | | | | | | |
| 1,2-Dodecanediol | | | | | | | |
| Stearyl alcohol | | | | | | | |
| Sangelose 90L | 0.2 | | 0.1 | 0.3 | 1.5 | 0.3 | |
| Sangelose 90M | | | | | | | 0.4 |
| Polysurf 67CS | | | | | | | |
| Ultragel 300 | | | | | | | |
| Metlose 90SH-04T | | | | | | | |
| Natrosol 250HR | | | | | | | |
| Adekanol GT-700 | | | | | | | |
| Polyox WSR301 | | | | | | | |
| Ion-exchange water | bal. | bal. | bal. | bal. | bal. | bal. | bal. |
| Total | 100.0 | 100.0 | 100.0 | 100.0 | 100.0 | 100.0 | 100.0 |
| Test results | | | | | | | |
| Viscosity (30° C.) [mPa·s] | 8100 | 45 | 5150 | 12700 | 145000 | 9600 | 3120 |
| Appearance stability (55° C., 2 wks) | ◯ | ◯ | ◯ | ◯ | ◯ | ◯ | ◯ |
| Appearance stability (5° C., 2 wks) | X | ◯ | ◯ | ◯ | ◯ | ◯ | ◯ |
| Anti-sticky sensation upon application | ◯ | ◯ | ◯ | ◯ | X | ◯ | ◯ |
| Suppleness after drying | Δ | Δ | ◯ | ◯ | Δ | Δ | ◯ |
| Smoothness after drying | Δ | ◯ | ◯ | ◯ | Δ | Δ | ◯ |

| Ingredients | Test Ex. 8 | 9 | 10 | 11 | 12 | 13 | 14 |
|---|---|---|---|---|---|---|---|
| | Amount (mass %) * blank: none | | | | | | |
| Dehyquart L80 | 2.0 | 2.0 | 2.0 | 2.0 | 2.0 | 2.0 | 2.0 |
| Stearyl trimethyl ammonium chloride | | | | | | | |
| POE(1.0)-1,2-dodecanediol | 3.0 | | 3.0 | | 3.0 | 3.0 | 3.0 |
| Aminon C-11S | | | | | | | |
| 1,2-Dodecanediol | | | | | | | |
| Stearyl alcohol | | | | | | | |
| Sangelose 90L | | | | | | | |
| Sangelose 90M | | | | | | | |
| Polysurf 67CS | 0.4 | | | | | | |

TABLE 1-continued

| | | | | | | | |
|---|---|---|---|---|---|---|---|
| Ultragel 300 | | 0.4 | 0.4 | 1.0 | | | |
| Metlose 90SH-04T | | | | | 0.5 | 1.0 | |
| Natrosol 250HR | | | | | | | 0.5 |
| Adekanol GT-700 | | | | | | | |
| Polyox WSR301 | | | | | | | |
| Ion-exchange water | bal. | bal. | bal. | bal. | bal. | bal. | bal. |
| Total | 100.0 | 100.0 | 100.0 | 100.0 | 100.0 | 100.0 | 100.0 |
| Test results | | | | | | | |
| Viscosity (30° C.) [mPa·s] | 4520 | 740 | 5120 | 12600 | 1700 | 5920 | 200 |
| Appearance stability (55° C., 2 wks) | ○ | ○ | ○ | ○ | X | X | X |
| Appearance stability (5° C., 2 wks) | ○ | ○ | ○ | ○ | X | X | X |
| Anti-sticky sensation upon application | ○ | ○ | ○ | X | Δ | X | X |
| Suppleness after drying | ○ | Δ | ○ | Δ | Δ | X | Δ |
| Smoothness after drying | ○ | Δ | ○ | X | X | X | X |

| | Test Ex. | | | | | |
|---|---|---|---|---|---|---|
| | 15 | 16 | 17 | 18 | 19 | 20 |
| Ingredients | Amount (mass %) * blank: none | | | | | |
| Dehyquart L80 | 2.0 | 2.0 | 2.0 | 2.0 | 2.0 | 2.0 |
| Stearyl trimethyl ammonium chloride | | | | | | |
| POE(1.0)-1,2-dodecanediol | 3.0 | | 3.0 | | | |
| Aminon C-11S | | | | 2.5 | | |
| 1,2-Dodecanediol | | | | | 3.0 | |
| Stearyl alcohol | | | | | | 3.0 |
| Sangelose 90L | | | | 0.3 | 0.2 | 0.1 |
| Sangelose 90M | | | | | | |
| Polysurf 67CS | | | | | | |
| Ultragel 300 | | | | | | |
| Metlose 90SH-04T | | | | | | |
| Natrosol 250HR | | | | | | |
| Adekanol GT-700 | 0.5 | 1.0 | | | | |
| Polyox WSR301 | | | 0.3 | | | |
| Ion-exchange water | bal. | bal. | bal. | bal. | bal. | bal. |
| Total | 100.0 | 100.0 | 100.0 | 100.0 | 100.0 | 100.0 |
| Test results | | | | | | |
| Viscosity (30° C.) [mPa·s] | 760 | 6520 | 250 | 5800 | 10500 | 15200 |
| Appearance stability (55° C., 2 wks) | ○ | ○ | ○ | ○ | ○ | X |
| Appearance stability (5° C., 2 wks) | ○ | ○ | ○ | ○ | X | ○ |
| Anti-sticky sensation upon application | X | X | X | ○ | ○ | ○ |
| Suppleness after drying | X | X | Δ | ○ | ○ | ○ |
| Smoothness after drying | X | X | Δ | ○ | Δ | ○ |

In Table 1 (also in Table 2), the employed commercial products are as follows:

Dehyquart L80: product of Cognis Japan (76% dicocoylethyl hydroxyethylmonium metosulfate, 24% propylene glycol)

Aminon C-11S: product of Kao (coconut fatty acid N-methylmonoethanolamide)

Sangelose-90L: product of Daido Chemical Corporation (100% stearoxy-modified hydroxypropylmethyl cellulose)

Sangelose-90M: product of Daido Chemical Corporation (100% stearoxy-modified hydroxypropylmethyl cellulose)

Polysurf 67CS: product of Aqualon (cetylhydroxyethyl cellulose)

Ultragel 300: product of Cognis (Polyquaternium-37 (92%) with water, isopropanol, 5Na diethylenetriaminepentaacetate)

Metolse 90SH-15T: product of Shin-Etsu Chemical (hydroxypropylmethyl cellulose)

Natrosol 250HR: product of Aqualon (hydroxyethyl cellulose)

Adekanol GT-700: product of Asahi Denka (100% PEG-240/HDI copolymer bis-decyltetradeceth-20 ether)

Polyox WSR301: product of Dow Chemical ((acrylic acid/alkyl (C10-30) acrylate) copolymer)

PEMELEN TR-1: product of B.F. Goodrich ((acrylic acid/alkyl (C10-30) acrylate) copolymer)

In Table 1, Test Example 1 sample, containing no ingredient (A), exhibited poor stability in appearance at low temperature. Test Example 2 sample, containing no ingredient (C), exhibited considerable low viscosity and poor viscoelasticity. Samples of Test Examples 3 and 4, falling within the preferred scope of the present invention, exhibited good test results. Test Example 5 sample, containing ingredient (C) in an amount in excess of the upper limit of the preferred range, exhibited a viscosity excessive to the target value and provided sticky sensation upon application thereof. Test Example 6, containing no ingredient (B), provided problematic sensation after drying. Samples of Test Examples 7 and 8, falling within the preferred scope of the present invention, exhibited good test results. Test Example 9, containing no ingredient (B), provided problematic sensation after drying. Test Example 10 sample, falling within the preferred scope of the present invention, exhibited good test results. Test Example 11, containing no ingredient (B), provided problematic sensation upon application and after drying. Samples of Test Examples 12 to 17, employing other ingredients (e.g., a thickener) instead of ingredient (C), exhibited poor results. Test Example 18 sample, falling within the preferred scope of the present invention, exhibited good test results. Test Example 19 sample, employing another ingredient instead of ingredient (B), exhibited poor stability in appearance, particularly at low temperature. Test Example 20 sample, employing another ingredient instead of ingredient (B), exhibited poor stability in appearance, particularly at high temperature.

TABLE 2

| | Test EX. | | |
|---|---|---|---|
| | 21 | 22 | 23 |
| Ingredients | Amount (mass %) * blank: none | | |
| Dehyquart L80 | 2.0 | | |
| POE(1.0)-1,2-dodecanediol | 3.0 | | |
| Sangelose 90L | 0.2 | | |
| Carboxyvinyl polymer | | 0.4 | 0.4 |
| Potassium hydroxide | | 0.2 | 0.25 |
| Polyoxyethylene hydrogenated castor oil | | 2.0 | |
| PEMULEN TR-1 | | | 0.20 |
| PEG-10 dimethicone | | 0.2 | 0.1 |
| Dimethyl polysiloxane (6 cs) | 3.0 | 3.0 | 3.0 |
| Dimethyl polysiloxane (20 cs) | 7.0 | 7.0 | 7.0 |
| Dimethyl silicone gum | 0.5 | 0.5 | 0.5 |
| Aminopropylmethicone | 0.5 | 0.5 | 0.5 |
| Ethanol | | 10.0 | 10.0 |
| Glycerin | | 2.0 | 2.0 |
| Dipropylene glycol | | 3.0 | 3.0 |
| Phenoxyethanol | 0.4 | 0.4 | 0.4 |
| Perfume | 0.1 | 0.1 | 0.1 |
| Ion-exchange water | bal. | bal. | bal. |
| Total | 100.0 | 100.0 | 100.0 |
| Test results | | | |
| Viscosity (30° C.) [mPa · s] | 9800 | 15000 | 24000 |
| Appearance stability (55° C., 2 wks) | ○ | ○ | ○ |
| Appearance stability (5° C., 2 wks) | ○ | ○ | ○ |
| Anti-sticky sensation upon application | ○ | Δ | Δ |
| Suppleness after drying | ○ | ○ | ○ |
| Smoothness after drying | ○ | X | X |

In Table 2, three Test Examples (Test Example 21 to 23) employed silicone oil. Among them, Test Example 21 (corresponding to Example) exhibited more favorable usability, as compared to that attained by Test Examples 22 and 23 (corresponding to Comparative Examples). When each of the samples of Test Examples 21 to 23 was applied to wet hair after, for example, shampooing, and then dried, Test Example 21 (corresponding to Example) provided more favorable hair suppleness and softness upon application and after drying, as compared to that attained by Test Examples 22 and 23 (corresponding to Comparative Examples).

In the case where each test sample was applied to shampooed hair followed by rinsed off and drying, Test Example 21 was found to exhibit more favorable usability, as compared to that attained by Test Examples 22 and 23. In other words, the samples of Test Examples 22 and 23 (corresponding to Comparative Examples) imparted no suppleness to hair during rinsing, and the rinsed hair had stiffness. The dried hair had no suppleness or smoothness. In contrast, the sample of Test Example 21 (corresponding to Example) imparted suppleness and softness to hair during and after rinsing, and the dried hair also had excellent suppleness and smoothness.

Hereinafter, Formulation Examples of the hair cosmetic composition of the present invention will be disclosed. Commercial products used in the Formulation Example are the same as described in relation to Table 1. Equivalent names listed in "Japanese Cosmetic Labeling Name" are also given. The formulations may be prepared through the method of the Test Examples or a method generally known in the art.

Formulation Example 1

Leave-on Hair Treatment

| Formulation | Amount (mass %) |
|---|---|
| Dehyquart L80 | 2.2 |
| POE(1.2)-1,2-dodecanediol | 5.0 |
| Dimethicone (50 cs) | 3.0 |
| Dimethicone (1,000,000 cs) | 0.5 |
| Aminopropylmethicone | 0.2 |
| Octyl palmitate | 0.1 |
| 2-Octyldodecanol | 0.1 |
| Phenoxyethanol | 0.4 |
| Sorbitol | 10.0 |
| Propylene glycol | 0.5 |
| Sodium L-glutamate | 0.1 |
| PEG-90M | 0.1 |
| Polysurf 67CS (Cetyl hydroxyethyl cellulose) | 0.3 |
| Ultragel 300 | 0.9 |
| Perfume | 0.2 |
| Ion-exchange water | bal. |
| Total | 100.0 |

Formulation Example 2

Rinse-Off Hair Treatment

| Formulation | Amount (mass %) |
|---|---|
| Dehyquart L80 | 3.0 |
| POE(0.8)-1,2-dodecanediol | 2.0 |
| Coconut fatty acid N-methylmonoethanolamide | 1.5 |
| Dimethicone (6 cs) | 10.0 |
| Dimethyl silicone gum | 0.3 |
| Amodimethicone | 0.5 |
| PEG amodimethicone | 0.1 |
| Isocetyl isostearate | 0.3 |
| Mineral oil | 0.6 |
| Methylparaben | 0.1 |
| Propylparaben | 0.1 |
| Glycerin | 8.0 |
| Dipropylene glycol | 0.5 |
| Sodium L-glutamate | 0.1 |
| Camellia oil | 0.1 |
| L-Arginine hydrochloride | 0.1 |
| Trimethylglycine | 0.05 |
| PCA-Na | 0.1 |
| Sangelose 90M (Stearoxy-modified hydroxypropyl methylcellulose) | 0.3 |
| Ultragel 300 | 0.9 |
| Dipotassium glycyrrhizinate | 0.1 |
| Orange oil | 0.1 |
| Royal jelly extract | 0.1 |
| Chamomile extract | 0.1 |
| Menthol | 0.2 |
| Capsicum tincture | 0.1 |
| Perfume | 0.2 |
| Ion-exchange water | bal. |
| Total | 100.0 |

Formulation Example 3

Hair Conditioner

| Formulation | Amount (mass %) |
|---|---|
| Dehyquart L80 | 1.5 |
| POE(1.0)-1,2-dodecanediol | 3.0 |
| Dimethicone (100 cs) | 10.0 |
| Dimethicone (10,000 cs) | 2.0 |
| Amodimethicone | 0.5 |
| PEG-10 dimethicone | 0.1 |
| PEG/PPG-14/7 dimethyl ether | 2.0 |
| Octoxyglycerin | 0.1 |
| 1,2-Octanediol | 0.1 |
| Isostearyl alcohol | 0.3 |
| Mineral oil | 0.5 |
| Methylparaben | 0.1 |
| Ethanol | 2.0 |
| 1,3-Butylene glycol | 1.0 |
| Sodium citrate | 0.1 |
| Cationized locust bean gum | 0.1 |
| Sangelose 60L (Stearoxy-modified hydroxypropyl methylcellulose) | 0.4 |
| Rosemary oil | 0.1 |
| t-Buthyl methoxydibenzoylmethane | 0.1 |
| Hydrolyzed wheat protein | 0.1 |
| Hydrolyzed wheat protein | 0.1 |
| Perfume | 0.2 |
| Ion-exchange water | bal. |
| Total | 100.0 |

The invention claimed is:

1. A hair cosmetic composition comprising the following ingredients (A), (B), (C), and (D):

(A) a di-long-chain cationic surfactant in an amount of 0.1 to 5 mass % with respect to the entirety of the hair cosmetic composition, said di-long-chain cationic surfactant being represented by formula (1):

[F1]

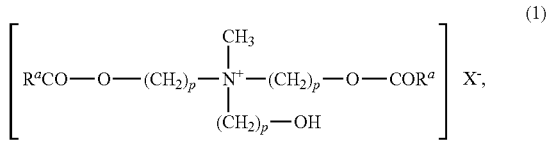

wherein each of $R^aCOs$, which may be identical to or different from each other, represents an aliphatic acyl group having 10 to 22 carbon atoms and 0 to 3 double bonds; p is an integer of 1 to 3; and X represents a halogen atom, metosulfate, or metophosphate;

(B) an ethylene oxide adduct of 1,2-alkanediol and/or an N-acyl-N-methylmonoethanolamide in an amount of 0.5 to 20 mass % with respect to the entirety of the hair cosmetic composition, said ethylene oxide adduct of 1,2-alkanediol being represented by formula (2):

[F2]

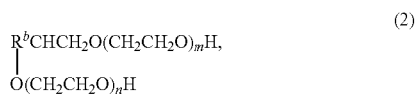

wherein $R^b$ represents a hydrocarbon group having 8 to 20 carbon atoms and 0 to 2 double bonds; each of m and n, which represent amount by mol of added ethylene oxide, is an integer of 0 to 2; and the average of m+n is greater than 0 and smaller than 2; and said N-acyl-N-methylmonoethanolamide being represented by formula (3):

[F3]

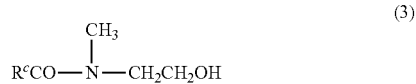

wherein $R^c$ represents a hydrocarbon group having 9 to 21 carbon atoms and 0 to 2 double bonds;

(C) a hydrophobicized alkyl cellulose in an amount of 0.01 to 1 mass% with respect to the entirety of the hair cosmetic composition; or a cationic polymer in an amount of 0.03 to 2 mass % with respect to the entirety of the hair cosmetic composition; or the hydrophobicized alkyl cellulose and the cationic polymer in a total amount of 0.03 to 1.5 mass % with respect to the entirety of the hair cosmetic composition, said hydrophobicized alkyl cellulose being represented by formula (4):

[F4]

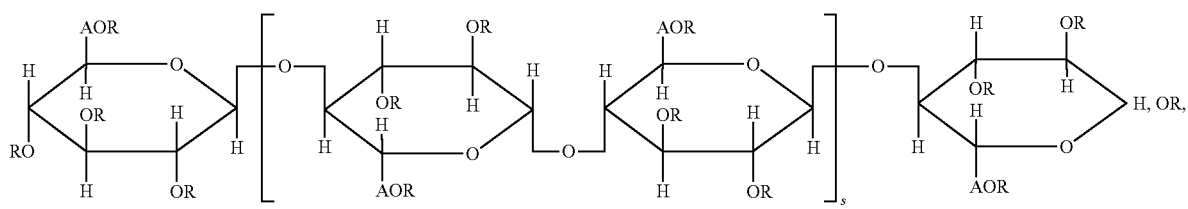

wherein R represents a bonding group $R^1$-$R^2$; a plurality of $R^1$s, which may be identical to or different from one another, represent at least one group selected from among —[CH$_2$CH (CH₃)O]ᵣ—, —[CH₂CH₂O]ᵣ—, and —[CH₂CH(OH)CH₂O]ᵣ—(wherein r is an integer of 0 to 4); R² represents at least one group selected from among a C12 to C28 hydrocarbon group, a hydrogen atom, and a C1 to C4 alkyl group, with at least one R² being a C12 to C28 hydrocarbon group; A represents a group —(CH₂)ₜ—(wherein t is an integer of 1 to 3); and s is a number of 100 to 10,000; and said cationic polymer being represented by formula (5):

[F5]

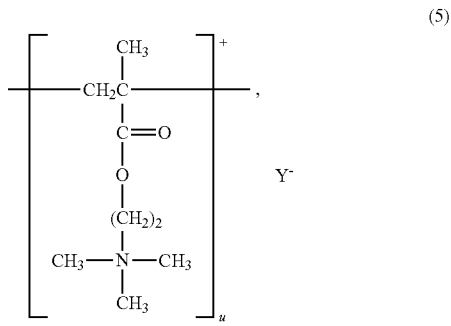

(5)

wherein Y represents a halogen atom, and u represents the number of bonded quaternary ammonium unit(s); and (D) water.

2. The hair cosmetic composition according to claim 1, wherein the RᵃCO of the di-long-chain cationic surfactant (1) has 10 to 14 carbon atoms.

3. The hair cosmetic composition according to claim 1, wherein the di-long-chain cationic surfactant (1) is dicocoyl-ethyl hydroxyethylmonium metosulfate.

4. The hair cosmetic composition according to claim 1, wherein the average of the sum of m and n is not less than 0.5 nor more than 1.5, each of m and n representing amount by mol of added ethylene oxide contained in the ethylene oxide adduct of 1,2-alkanediol (2).

5. The hair cosmetic composition according to claim 1, wherein each of $R^b$CHCH₂ of the ethylene oxide adduct of 1,2-alkanediol (2) and $R^c$CO of the N-acyl-N-methylmonoethanolamide (3) has 10 to 14 carbon atoms.

6. The hair cosmetic composition according to claim 1, wherein the hydrophobicized alkyl cellulose (4) is stearoxyhydroxypropylmethyl cellulose or stearoxyhydroxyethyl cellulose.

7. The hair cosmetic composition according to claim 1, which further contains an oil ingredient.

8. The hair cosmetic composition according to claim 1, which is a hair conditioner, a hair rinse, a hair treatment, or a rinse-in-shampoo.

9. The hair cosmetic composition according to claim 1, which is used without rinsing off the composition after application thereof to hair.

* * * * *